United States Patent
Han et al.

(10) Patent No.: US 11,921,066 B2
(45) Date of Patent: Mar. 5, 2024

(54) SYSTEM FOR ULTRA-HIGH TEMPERATURE IN-SITU FRETTING FATIGUE EXPERIMENT

(71) Applicant: NANJING UNIVERSITY OF AERONAUTICS AND ASTRONAUTICS, Jiangsu (CN)

(72) Inventors: Qinan Han, Jiangsu (CN); Xiaolin Yang, Jiangsu (CN); Haitao Cui, Jiangsu (CN); Yue Su, Jiangsu (CN); Huiji Shi, Jiangsu (CN)

(73) Assignee: NANJING UNIVERSITY OF AERONAUTICS AND ASTRONAUTICS, Nanjing (CN)

(*) Notice: Subject to any disclaimer, the term of this patent is extended or adjusted under 35 U.S.C. 154(b) by 456 days.

(21) Appl. No.: 17/231,009

(22) Filed: Apr. 15, 2021

(65) Prior Publication Data

US 2021/0285901 A1 Sep. 16, 2021

Related U.S. Application Data

(63) Continuation of application No. PCT/CN2020/118831, filed on Sep. 29, 2020.

(30) Foreign Application Priority Data

Mar. 11, 2020 (CN) .......................... 202010167112.1

(51) Int. Cl.
  *G01N 23/2251* (2018.01)
  *G01N 23/2204* (2018.01)
  *G01N 33/204* (2019.01)

(52) U.S. Cl.
  CPC ..... *G01N 23/2251* (2013.01); *G01N 23/2204* (2013.01); *G01N 33/204* (2019.01);
  (Continued)

(58) Field of Classification Search
  CPC .......... G01N 23/2251; G01N 23/2204; G01N 33/204; G01N 2291/0234;
  (Continued)

(56) References Cited

U.S. PATENT DOCUMENTS 3,381,526 A * 5/1968 Rastogi .................... G01N 3/32
  73/810
3,427,873 A * 2/1969 Mehdizadeh ............ G01N 3/32
  73/809

(Continued)

FOREIGN PATENT DOCUMENTS

CN 104913981 A 9/2015
CN 105092387 A 11/2015
(Continued)

OTHER PUBLICATIONS

The Second Office Action in counterpart Chinese Application No. 202010167112.1, dated Aug. 31, 2021.

*Primary Examiner* — Suman K Nath

(57) ABSTRACT

A system for ultra-high temperature in-situ fretting fatigue experiment, includes a heat preservation cover defining a, a heating device arranged in the mounting space, a first test sample, a second test sample, and a clamping device arranged in the mounting space. The first test sample and the second test sample are arranged at an upper end of the heating device along a horizontal direction. A mortise is formed at an end of the first test sample facing towards the second test sample. A tenon mating with the mortise is formed at an end of the second test sample facing towards the first test sample. The clamping device is configured to be clamped at two ends of the mated first test sample and second test sample and to apply a periodically reciprocating loading along a length direction of the first test sample and the second test sample.

10 Claims, 7 Drawing Sheets

(52) U.S. Cl.
CPC ............... *G01N 2203/0073* (2013.01); *G01N 2291/0234* (2013.01)

(58) Field of Classification Search
CPC ... G01N 2203/0073; G01N 2203/0057; G01N 2203/0226; G01N 2203/0234; G01N 2203/0647; G01N 3/32; G01N 33/20; H01J 37/20; H01J 2237/2813; H01J 2237/2065
See application file for complete search history.

(56) References Cited

U.S. PATENT DOCUMENTS

| | | | | |
|---|---|---|---|---|
| 5,710,426 | A * | 1/1998 | Reed | G01N 3/18 250/237 G |
| 2016/0116387 | A1* | 4/2016 | Houze | G01N 3/32 73/808 |
| 2020/0191702 | A1* | 6/2020 | Williams | G01N 17/002 |

FOREIGN PATENT DOCUMENTS

| | | |
|---|---|---|
| CN | 105209882 A | 12/2015 |
| CN | 207516011 U | 6/2018 |
| CN | 109827735 A | 5/2019 |
| CN | 110823713 A | 2/2020 |
| CN | 111443103 A | 7/2020 |
| EP | 1602914 A2 | 12/2005 |

* cited by examiner

A-A

SYSTEM FOR ULTRA-HIGH TEMPERATURE IN-SITU FRETTING FATIGUE EXPERIMENT

CROSS-REFERENCE TO RELATED APPLICATION

The present application is a continuation of International Application No. PCT/CN2020/118831 filed Sep. 29, 2020, which claims priority to Chinese Patent Application No. 202010167112.1, filed on Mar. 11, 2020, the entire disclosure of which are hereby incorporated herein by reference.

TECHNICAL FIELD

The present disclosure relates to the technical field of aeroengine, and more particularly, to a system for ultra-high temperature in-situ fretting fatigue experiment.

BACKGROUND

An operating temperature of an aeroengine turbine determines performance of the entire engine, thus affecting performance of an entire aircraft. Nickel-based superalloys, due to their excellent high-temperature mechanical properties, are widely used in manufacture of aeroengine turbine blades. At present, a joint between a turbine blade and a turbine disk is a mortise-tenon joint. This tenon joint can generate alternating axial and normal loads during a rotation of turbine blades, and can also produce small amplitude alternating motion in a contact region, i.e., a phenomenon of fretting fatigue.

According to statistics from the literature, more than one-sixth of aeroengine failures caused by fatigue are resulted from fretting fatigue. And once a fatigue failure of blades occurs, unpredictable accidents will occur. As a result, it is of great significance to study fretting fatigue properties of nickel-based superalloys at a service temperature. A turbine inlet temperature may often be more than 1,100 degrees Celsius. Therefore, for studying fretting fatigue of blade-tenon joint, it has important theoretical and engineering value to design a system for in-situ fretting fatigue experiment at an ultra-high temperature and to real-time observe a damage failure process of materials during a fretting fatigue process.

In recent years, the fretting fatigue properties of nickel-based superalloys have been extensively studied. However, in order to study the fretting fatigue properties of nickel-based superalloys at an ultra-high temperature (above 700° C.), a problem to be solved is how to raise a temperature of a test sample during an experiment to 700° C. or higher. If an improper heating method is used, hot electrons may be generated in a vacuum chamber, which will affect a secondary electron reception of an in-situ scanning electron microscope (SEM). In this way, an image becomes blurry, and it is difficult to make a real-time observation.

SUMMARY

The present disclosure aims to solve at least one of the technical problems in the related art. To this end, an objective of the present disclosure is to provide a system for ultra-high temperature in-situ fretting fatigue experiment. The system for ultra-high temperature in-situ fretting fatigue experiment may simulate a basic construction of a contact between a turbine blade and a turbine disk, has a simple structure, and is easy to operate.

According to an embodiment of the system for ultra-high temperature in-situ fretting fatigue experiment, the system for ultra-high temperature in-situ fretting fatigue experiment includes a heat preservation cover, a heating device, a first test sample, a second test sample, and a clamping device. The heat preservation cover defines a mounting space. The heating device is arranged in the mounting space. The first test sample is made of a nickel-based polycrystal superalloy to simulate a turbine disk. A second test sample is made of a nickel-based single-crystal superalloy to simulate a turbine blade. The first test sample and the second test sample are arranged at an upper end of the heating device along a horizontal direction. A mortise is formed at an end of the first test sample facing towards the second test sample. A tenon configured to mate with the mortise is formed at an end of the second test sample facing towards the first test sample. A clamping device is arranged in the mounting space. The clamping device is configured to be clamped at two ends of the mated first test sample and second test sample, and configured to apply a periodically reciprocating loading along a length direction of the first test sample and the second test sample.

In the system for ultra-high temperature in-situ fretting fatigue experiment according to the embodiment of the present disclosure, by arranging the first test sample and the second test sample at the upper end of the heating device along the horizontal direction, and by arranging the observation hole on an upper side of the heat preservation cover, the heating device can not only heat the first test sample and the second test sample easily, but also support the first test sample and the second test sample in such a manner that the first test sample and the second test sample can be more stable in the high-temperature heat preservation cover. In the meantime, hot electrons generated by heat radiation in the heat preservation cover may be also reduced, which improves imaging clarity of an observation instrument in a high temperature environment, thereby allowing to observe a damage failure process of the first test sample and the second test sample during a fretting fatigue process more clearly.

In addition, by forming the mortise at the end of the first test sample facing towards the second test sample and forming the tenon configured to mate with the mortise at the end of the second test sample facing towards the first test sample, the first test sample and the second test sample can simulate an actual joint between the turbine blade and the turbine disk. Consequently, the first test sample and the second test sample can produce a typical fretting fatigue condition. During the experiment, an evolutionary process a fretting fatigue damage of the first test sample and the second test sample in a high temperature environment can be observed only by observing two symmetrical contact regions of the mortise and the tenon, which is simple in operations, also saves time for the experiment, reduces the costs, and improves the experiment accuracy. Therefore, the system for ultra-high temperature in-situ fretting fatigue experiment according to the embodiment of the present disclosure requires a simple device structure, which not only reduces the difficulty of assembly, but also improves the accuracy of experimental results.

In addition, the system for ultra-high temperature in-situ fretting fatigue experiment according to the present disclosure may also have the following additional technical features.

In some embodiments of the present disclosure, an observation hole in communication with the mounting space is formed on the heat preservation cover, the observation hole is located in a middle part of a length direction of the heat preservation cover, and the first test sample and the second test sample are mated with each other and movably arranged in the mounting space in such a manner that the mortise and the tenon are located right below the observation hole.

In an embodiment, in a direction from the first test sample towards the second test sample, the first test sample sequentially includes a first clamping portion, a first connecting portion, and a first mating portion. A width of the first connecting portion is smaller than a width of the first clamping portion and a width of the first mating portion, and the mortise is formed on the first mating portion to open towards the second test sample.

In some embodiments of the present disclosure, in a direction from the second test sample towards the first test sample, the second test sample sequentially includes a second clamping portion, a second connecting portion, and a second mating portion. A width of the second connecting portion is smaller than a width of the second clamping portion and a width of the second mating portion, and the second mating portion is formed by the tenon.

In some embodiments of the present disclosure, the heating device includes a temperature control device, a heating wire, and a gasket. The temperature control device is configured to adjust a temperature of the heating wire. The first test sample and the second test sample are disposed on the gasket. The gasket is configured to transfer heat generated by the heating wire towards the first test sample and the second test sample.

In an embodiment, the heating wire is arranged at a lower end of the gasket.

In an embodiment, in a length direction of the heat preservation cover, a length of the gasket is greater than or equal to a total length of the mated first test sample and second test sample.

In an embodiment, the gasket includes two supporting portions spaced apart from each other along the length direction of the first test sample and the second test sample, and an interconnecting portion connected to the two supporting portions. One of the two supporting portions is located at an end of the first test sample facing away from the second test sample, the other one of the two supporting portions is located at an end of the second test sample facing away from the first test sample. The first test sample and the second test sample are disposed on the interconnecting portion.

In an embodiment, the interconnecting portion is formed as a hollow ring located at a position where the first test sample and the second test sample are mated with each other.

In an embodiment, the gasket is made of a special high-temperature resistant material.

In some embodiments of the present disclosure, in a length direction of the heat preservation cover, a length of the first test sample is equal to a length of the second test sample.

In an embodiment, the system for ultra-high temperature in-situ fretting fatigue experiment further includes a SEM observation cavity and a vacuum device. The vacuum device is configured to form a vacuum state in the SEM observation cavity.

Additional aspects and advantages of the present disclosure will be given at least in part in the following description, or become apparent at least in part from the following description, or can be learned from practicing of the present disclosure The technical solutions of the present disclosure will be further described in detail below through the accompanying drawings and embodiments.

BRIEF DESCRIPTION OF DRAWINGS

The above and/or additional aspects and advantages of embodiments of the present disclosure will become apparent and readily appreciated from the following description with reference to the accompanying drawings, in which.

REFERENCE SIGNS

Figure 1:
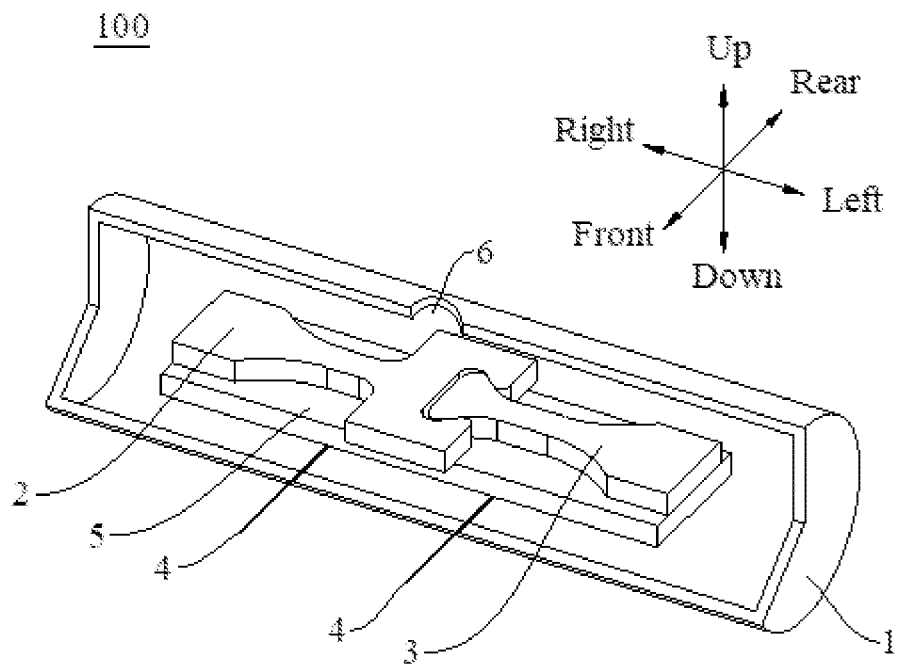
FIG. 1 is a schematic structural diagram, observing from one angle, of a heat preservation cover, a first test sample, a second test sample, a heating wire, a gasket, and an observation hole of a system for ultra-high temperature in-situ fretting fatigue experiment according to an embodiment of the present disclosure.
Figure 2:
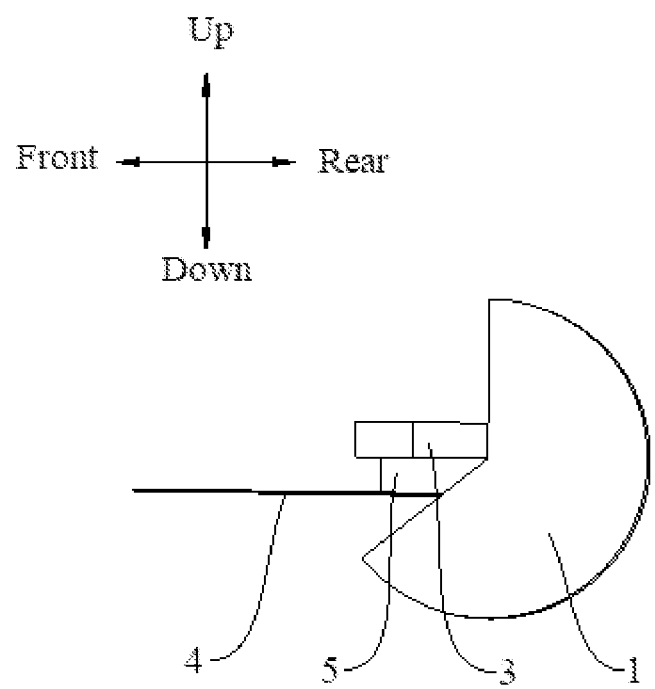
FIG. 2 is a schematic structural diagram, observing from another angle, of a heat preservation cover, a first test sample, a second test sample, a heating wire, a gasket, and an observation hole of a system for ultra-high temperature in-situ fretting fatigue experiment according to an embodiment of the present disclosure.

100: system for ultra-high temperature in-situ fretting fatigue experiment
1: heat preservation cover; 2: first test sample; 21: first clamping portion; 22: first connecting portion; 23: first mating portion; 24: mortise; 25: first friction surface; 3: second test sample; 31: second clamping portion; 32: second connecting portion; 33: tenon; 34: second friction surface; 4: heating wire; 5: gasket; 51: supporting portion; 52: interconnecting portion; 6: observation hole.

DESCRIPTION OF EMBODIMENTS

The embodiments of the present disclosure will be described in detail below with reference to examples thereof as illustrated in the accompanying drawings, throughout which same or similar elements or elements having same or similar functions are denoted by same or similar reference numerals. The embodiments described below with reference to the drawings are illustrative only, and are intended to explain, rather than limiting, the present disclosure.

In the description of the present disclosure, it is to be understood that, terms such as "length", "width", "thickness", "over", "below", "front", "back", "left", "right", "vertical", "horizontal", "bottom", and "axial" refer to directions and location relations which are the directions and location relations shown in the drawings, and for describing the present disclosure and for describing in simple, and which are not intended to indicate or imply that the device or the elements are disposed to located in the specific orientations or are structured and performed in the specific orientations, which could not to be understood as limitations of the present disclosure. In addition, the feature defined with "first" and "second" may include one or more this feature distinctly or implicitly. In the description of the present disclosure, "a plurality of" means two or more than two, unless specified otherwise.

In the description of the present disclosure, it is to be understood that, unless specified or limited otherwise, terms "mounted," "connected," and "coupled" are understood broadly, such as fixed, detachable or integrated mountings, joints and couplings, and can be mechanical or electrical mountings, joints and couplings, and also can be direct and via media indirect mountings, joints, and couplings, and further can be inner mountings, joints and couplings of two components. For those skilled in the art, specific meanings of the above terms in the present disclosure can be understood under specific circumstances.

A system 100 for ultra-high temperature in-situ fretting fatigue experiment according to an embodiment of the present disclosure is described below with reference to FIGS. 1 to 6.

As illustrated in FIGS. 1 to 6, the system 100 for ultra-high temperature in-situ fretting fatigue experiment according to the embodiment of the present disclosure includes a heat preservation cover 1, a heating device, a first test sample 2, a second test sample 3, and a clamping device.

As an example, the heat preservation cover 1 defines a mounting space, and the heating device can be provided in the mounting space. In this way, after the heating device is fitted in the mounting space, the heat preservation cover 1 may store the heat released by the heating device. In this way, the heating device may raise a temperature in the heat preservation cover 1 to an expected temperature quickly, and the heat preservation cover 1 can ensure that the system 100 for ultra-high temperature in-situ fretting fatigue experiment is maintained in a high temperature environment once the expected temperature is reached, thereby simulating an actual high temperature environment, and accordingly, improving authenticity and accuracy of experimental data.

It can be understood that the heat preservation cover 1 may be made of a high-temperature resistant material to protect the heat preservation cover 1 from being oxidized or corroded in a high temperature environment for a long time. A shape of the heat preservation cover 1 may be designed based on actual conditions, and is not limited herein. For example, as illustrated in FIG. 1, the heat preservation cover 1 may extend in a left-right direction, thereby forming a cylindrical structure. The cylinder defines a mounting space.

The first test sample 2 is made of a nickel-based polycrystal superalloy to simulate a turbine disk. That is, the first test sample 2 can be made of a nickel-based polycrystal superalloy material, which is consistent with the common material for the turbine disk in the actual aeroengine turbines, such that the experimental data may be more accurate. In addition, the nickel-based polycrystal superalloy material has high strength and good oxidation- and gas corrosion-resistance capability at a temperature in a range of 650 to 1000° C. Thus, the parameters required by a fatigue experiment, e.g., fretting fatigue life data, can be measured by testing the first test sample 2 in the high temperature environment.

The second test sample 3 is made of a nickel-based single-crystal superalloy to simulate a turbine blade. That is, the second test sample 3 can be made of a nickel-based single-crystal superalloy material, which is also consistent with the common material for the turbine blade in the actual aeroengine turbines, such that the experimental data may be more accurate. In addition, the nickel-based single-crystal superalloy material has excellent mechanical properties at high temperature, such that the parameters required by the fatigue experiment, e.g., the fretting fatigue life data, can be measured by testing the second test sample 3 in the high temperature environment, thereby improving experimental efficiency and accuracy of the fatigue experiment.

The first test sample 2 and the second test sample 3 are arranged at an upper end of the heating device along a horizontal direction. For example, as illustrated in FIG. 1, the first test sample 2 extends along the left-right direction, and the second test sample 3 also extends along the left-right direction, such that extension directions of the first test sample 2 and the second test sample 3 are parallel to an extension direction of the heat preservation cover 1, i.e., parallel to a length direction. In this way, the first test sample 2 and the second test sample 3 can be mated in the heat preservation cover 1 more conveniently. Further, after the first test sample 2 and the second test sample 3 are mated at the upper end of the heating device, the heating device can not only heat the first test sample 2 and the second test sample 3 more easily, but also support the first test sample 2 and the second test sample 3, such that the first test sample 2 and the second test sample 3 can be more stable in the high-temperature heat preservation cover 1. Consequently, a simulation of fretting fatigue conditions of the first test sample 2 and the second test sample 3 in the high temperature environment may be observed more conveniently.

In the related art, a test sample is heated by a heating piece surrounding the test sample. After the heating piece is heated, a large number of hot electrons may be generated around the test sample. The hot electrons may affect an imaging effect of an observation instrument, e.g., SEM, for observing the test sample. That is, the imaging of the observation instrument is not clear in the high temperature environment, which makes it difficult to observe a microstructure of a surface of the test sample. By mating the first test sample 2 and the second test sample 3 above the heating device and arranging the observation hole 6 on the upper side of the heat preservation cover 1, the heating device can be away from the observation instrument at the observation hole 6. In this way, the influence of the hot electrons generated by thermal radiation on the observation instrument can be reduced, without affecting the heating processing of the first test sample 2 and the second test sample 3 by the heating device. Thus, the imaging clarity of the observation instrument in the high temperature environment can be improved, allowing a real-time observation of the damage failure process of surfaces of the first test sample 2 and the second test sample 3 during the fretting fatigue process.

Further, a mortise 24 is formed at an end of the first test sample 2 facing towards the second test sample 3, and a tenon 33 mating with the mortise 24 is formed at an end of the second test sample 3 facing towards the first test sample 2. In this manner, the first test sample 2 simulates a real contact outlook of the turbine disk, and the second test sample 3 simulates a real contact outlook of the turbine blade. When the tenon 33 is engaged in the mortise 24, the first test sample 2 and the second test sample 3 forms a tenon joint. As a result, the first test sample 2 and the second test sample 3 can simulate the actual joint between the turbine blade and the turbine disk, and thus the first test sample 2 and the second test sample 3 can form a typical fretting fatigue condition.

Figure 5:
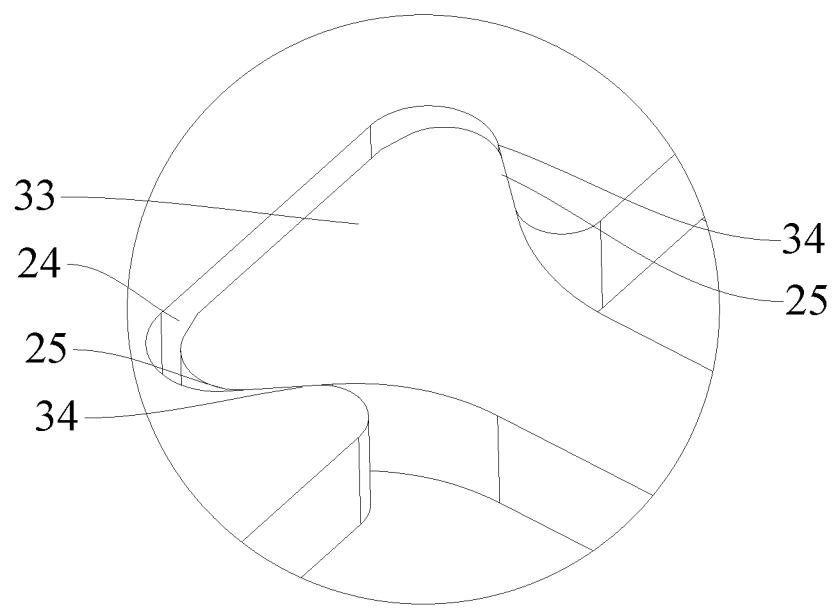
FIG. 5 is an enlarged view of a region A in FIG. 4.

When the mortise 24 of the first test sample 2 is mated with the tenon 33 of the second test sample 3, the first test sample 2 and the second test sample 3 are mutually movable. As an example, the first test sample 2 and the second test sample 3 may move in a direction facing away from each other, such that the mortise 24 and the tenon 33 may contact with each other and generate friction. For example, as illustrated in FIG. 5, a first friction surface 25 may be formed on the mortise 24, and a second friction surface 34 may be formed on the tenon 33. When the first test sample 2 and the second test sample 3 move in the direction facing away from each other, the first friction surface 25 and the second friction surface 34 contact each other and generate friction. In this case, an evolutionary process a fretting fatigue damage of the first test sample 2 and the second test sample 3 in a high temperature environment can be observed only by observing two symmetrical contact regions of the mortise 24 and the tenon 33, which is simple in operations, also saves time for the experiment, experiment, reduces the costs, and improves the experiment accuracy.

Figure 4:
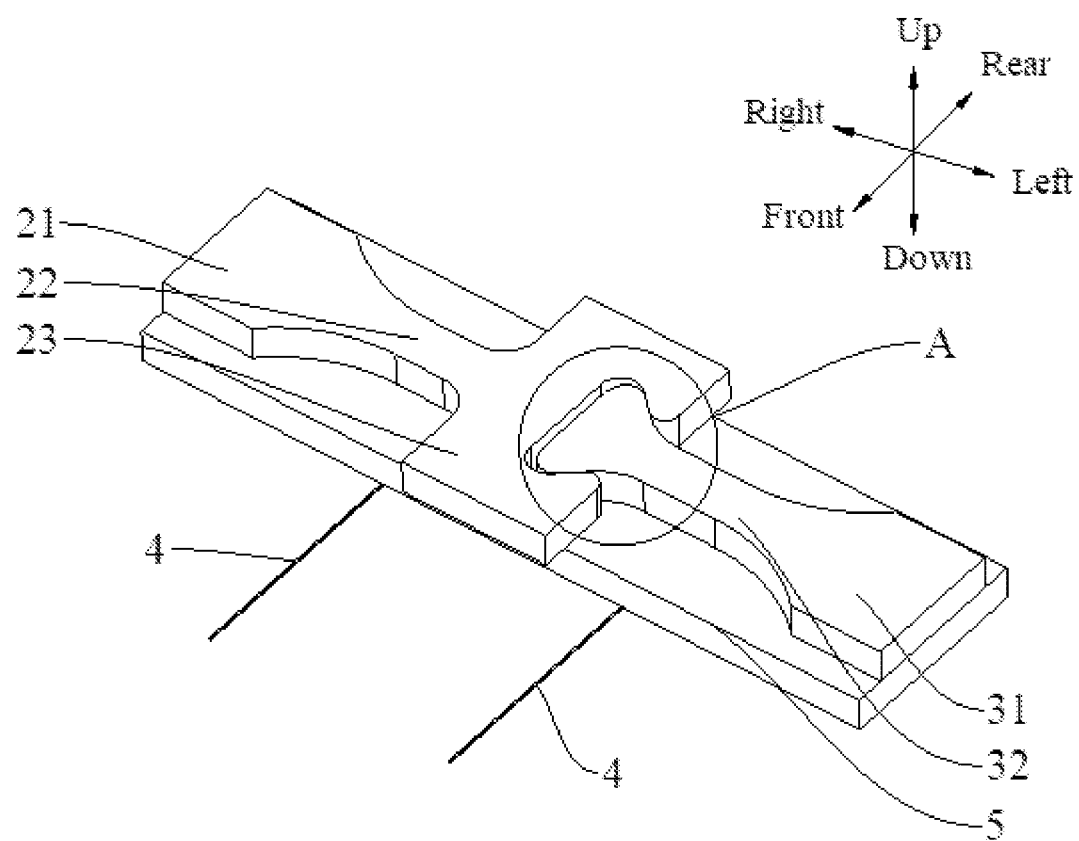
FIG. 4 is a schematic structural diagram of a first test sample, a second test sample, a heating wire, and a gasket of a system for ultra-high temperature in-situ fretting fatigue experiment according to an embodiment of the present disclosure.

The clamping device is arranged in the mounting space, and the clamping device is configured to be clamped at two ends of the mated first test sample 2 and the second test sample 3 and configured to apply periodically reciprocating loading along a length direction of the first test sample 2 and the second test sample 3. That is, the clamping device may be fitted in the mounting space. After the clamping device is fitted in the mounting space, the clamping device can clamp the first test sample 2 and the second test sample 3 in the mounting space more easily. As an example, when the first test sample 2 and the second test sample 3 are mated with each other, one end of the clamping device is clamped on an end of the first test sample 2 facing away from the second test sample 3, and the other end of the clamping device is clamped on an end of the second test sample 3 facing away from the first test sample 2. When the clamping device is clamped on the first test sample 2 and the second test sample 3, the clamping device can generate a force along a rightward direction as illustrated in FIG. 4 on the first test sample 2, and in the meantime, the clamping device can also generate a force along a leftward direction as illustrated in FIG. 4 on the second test sample 3. In this way, the first test sample 2 and the second test sample 3 move away from each other, and thus the first friction surface 25 and the second friction surface 34 may contact with each other and generate friction. Further, the forces of the clamping device applying on the first test sample 2 and the second test sample 3 may satisfy a cosine function. That is, the forces of the clamping device applying on the first test sample 2 and the second test sample 3 may change with time. The forces may gradually increase and then gradually decrease with time. In this way, the first test sample 2 and the second test sample 3 may simulate an actual loading condition of the turbine blade and the turbine disk in an aeroengine turbine.

In the system 100 for ultra-high temperature in-situ fretting fatigue experiment according to the embodiment of the present disclosure, by arranging the first test sample 2 and the second test sample 3 at the upper end of the heating device along the horizontal direction, and by arranging the observation hole 6 on an upper side of the heat preservation cover 1, the heating device can not only heat the first test sample 2 and the second test sample 3 easily, but also support the first test sample 2 and the second test sample 3 in such a manner that the first test sample 2 and the second test sample 3 can be more stable in the high-temperature heat preservation cover 1. In the meantime, the hot electrons generated by heat radiation in the heat preservation cover 1 may be also reduced, which improves the imaging clarity of an observation instrument such as SEM in a high temperature environment, thereby allowing to observe a damage failure process of the first test sample 2 and the second test sample 3 during a fretting fatigue process more clearly.

In addition, by forming the mortise 24 at the end of the first test sample 2 facing towards the second test sample 3 and forming the tenon 33 configured to mate with the mortise 24 at the end of the second test sample 3 facing towards the first test sample 2, the first test sample 2 and the second test sample 3 can simulate an actual joint between the turbine blade and the turbine disk. Consequently, the first test sample 2 and the second test sample 3 can produce a typical fretting fatigue condition. During the experiment, an evolutionary process a fretting fatigue damage of the first test sample 2 and the second test sample 3 in a high temperature environment can be observed only by observing two symmetrical contact regions of the mortise 24 and the tenon 33, which is simple in operations, also saves time for the experiment, experiment, reduces the costs, and improves the experiment accuracy. Therefore, the system 100 for ultra-high temperature in-situ fretting fatigue experiment according to the embodiment of the present disclosure requires a simple device structure, which not only reduces the difficulty of assembly, but also improves the accuracy of experimental results.

In some embodiments of the present disclosure, the observation hole 6 in communication with the mounting space is formed on the heat preservation cover 1. The observation hole 6 is located in a middle part of a length direction of the heat preservation cover 1. The first test sample 2 and the second test sample 3 are mated with each other and movably arranged in the mounting space in such a manner that the mortise 24 and the tenon 33 can be located right below the observation hole 6.

Figure 3:
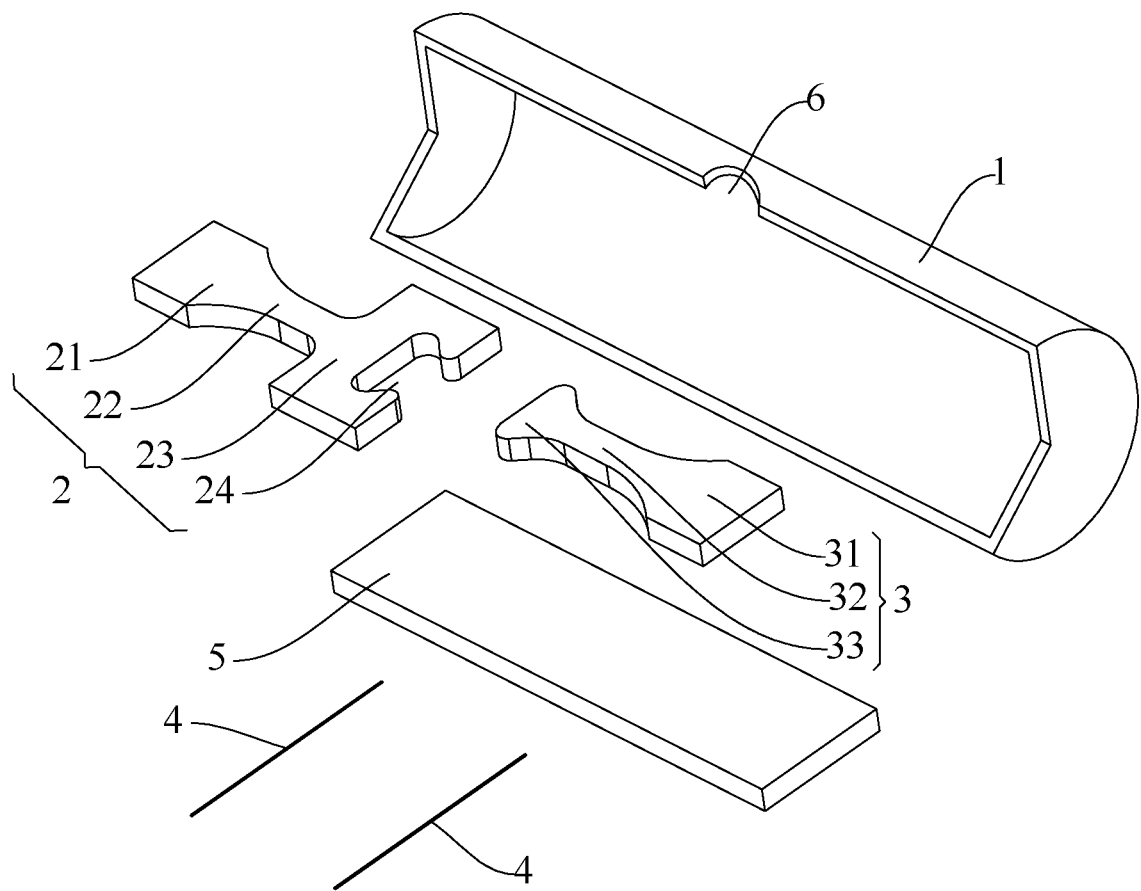
FIG. 3 is an exploded view of a heat preservation cover, a first test sample, a second test sample, a heating wire, a gasket, and an observation hole of a system for ultra-high temperature in-situ fretting fatigue experiment according to an embodiment of the present disclosure.

For example, as illustrated in FIG. 1 and FIG. 3, the observation hole 6 is provided on the heat preservation cover 1, and the observation hole 6 is located on a perpendicular bisector of a left-right direction of the heat preservation cover 1. Since the observation hole 6 is in communication with the mounting space, the fretting fatigue process of the first test sample 2 and the second test sample 3 in the heat preservation cover 1 can be observed through the observation hole 6. Further, the first test sample 2 and the second test sample 3 are movable in the mounting space. Therefore, during the experiment, the clamping device can be moved by controlling a moving handle, such that the first test sample 2 and the second test sample 3 connected to the clamping device can be translated. In this way, the front and rear contact regions between the first test sample 2 and the second test sample 3 are located right below the observation hole 6, thereby allowing the observation of the fretting contact region. Therefore, the observation instrument may timely photograph and save the entire process of crack initiation and propagation of the mortise 24 and the tenon 33.

In an example, the moving handle may be electrically connected to the heating device. Thus, the heating device may be moved in the heat preservation cover 1 by controlling the moving handle. As a result, the mortise 24 and the tenon 33 may be moved to right below the observation hole 6 for observation.

In an embodiment, in a direction from the first test sample 2 towards the second test sample 3, the first test sample 2 is sequentially divided into a first clamping portion 21, a first connecting portion 22, and a first mating portion 23. A width of the first connecting portion 22 is smaller than a width of the first clamping portion 21 and a width of the first mating portion 23. The mortise 24 is formed on the first mating portion 23 to open towards the second test sample 3.

For example, as illustrated in FIG. 4, one end of the first connecting portion 22 is connected to the first clamping portion 21, and the other end of the first connecting portion 22 is connected to the first mating portion 23. By setting a vertical cross-sectional area of the first clamping portion 21 to be greater than a vertical cross-sectional area of the first connecting portion 22, the clamping device can clamp the first clamping portion 21 more easily. By setting a vertical cross-sectional area of a first mating portion to be greater than the vertical cross-sectional area of the first connecting portion 22, the mortise 24 can be provided on the first fitting portion 23 conveniently. A size of the mortise 24 can be designed according to a size of the tenon 33.

In another embodiment, in a direction from the second test sample 3 towards the first test sample 2, the second test sample 3 is sequentially divided into a second clamping portion 31, a second connecting portion 32, and a second mating portion. A width of the second connecting portion 32 is smaller than a width of the second clamping portion 31 and a width of the second mating portion. The second mating portion is formed by the tenon 33.

For example, as illustrated in FIG. 4, one end of the second connecting portion 32 is connected to the second clamping portion 31, and the other end of the second connecting portion 32 is connected to the second mating portion. By setting a vertical cross-sectional area of the second clamping portion 31 to be greater than a vertical cross-sectional area of the second connecting portion 32, the clamping device can clamp the second clamping portion 31 more easily. By setting a vertical cross-sectional area of a second mating portion to be greater than the vertical cross-sectional area of the second connecting portion 32, the tenon 33 can be designed according to a size of the mortise 24, and the tenon 33 can mate with the mortise 24 more conveniently.

In some embodiments of the present disclosure, the heating device includes a temperature control device, a heating wire 4 and a gasket 5. The temperature control device is configured to adjust a temperature of the heating wire 4. That is, the heating wire 4 may be connected to the temperature control device. When the heating wire 4 is connected to the temperature control device, the temperature control device may conduct heat to the heating wire 4 and control the temperature of the heating wire 4, such that the temperature control device can control a temperature in the heat preservation cover 1. When the temperature of the heating wire 4 does not reach an expected value, the temperature control device can continuously heat the heating wire 4. When the temperature of the heating wire 4 reaches the expected value, the temperature control device can stop heating the heating wire 4. By heating the heating wire 4 with the temperature control device, it is simple to operate, allows the heating temperature to be more accurate, and provides a stable high temperature environment for the experiment, thereby improving the accuracy of the experimental data.

Further, the first test sample 2 and the second test sample 3 are configured to be placed on the gasket 5. The gasket 5 is configured to transfer the heat generated by the heating wire 4 towards the first test sample 2 and the second test sample 3. For example, as illustrated in FIG. 4, the gasket 5 may be disposed between the heating wire 4 and the first test sample 2 and the second test sample 3. In this way, the heating wire 4 can transfer heat to the gasket 5. After the heat is transferred to the gasket 5, the gasket 5 can transfer the heat to the first test sample 2 and the second test sample, so as to heat the first test sample 2 and the second test sample 3. The heating wire 4 is continuously heated by the temperature control device, until the first test sample 2 and the second test sample 3 reach the expected value of temperature. In this way, the high temperature environment is produced in the heat preservation cover 1, and the contact regions between the first test sample 2 and the second test sample 3 can produce fretting fatigue damage failures, cracks, etc.

Instead of the heating with the heating wire 4 directly attached to the first test sample 2 and the second test sample 3, the gasket 5 is used for heating. Since the heating wire 4 has a small diameter, the heat may be concentrated in a region where the heating wire 4 is attached. In the present disclosure, the heating wire 4 is attached to the gasket 5, and the gasket 5 then transfers heat to the first test sample 2 and the second test sample 3, allowing a uniform heating of the first test sample 2 and the second test sample 3.

In an embodiment, the heating wire 4 is arranged at a lower end of the gasket 5. In this way, by arranging the heating wire 4 below the gasket 5 and by arranging the observation hole 6 above the first test sample 2 and the second test sample 3, the observation instrument can be less interfered by the hot electrons in the heat preservation cover 1. In this way, in the high temperature environment, the observation instrument at the observation hole 6 may produce a clear image, thereby improving the accuracy of the experiment. It can be appreciated that the gasket 5 is required to support the first test sample 2 and the second test sample 3. Thus, a shape of the gasket 5 may be designed based on shapes and sizes of the first test sample 2 and the second test sample 3, which is not limited in the present disclosure.

In an embodiment, in a length direction of the heat preservation cover 1, a length of the gasket 5 is greater than or equal to a sum of lengths of the mated first test sample 2 and second test sample 3. In other words, the mortise 24 of the first test sample 2 and the tenon 33 of the second test sample 3 are mated with each other and disposed on the gasket 5. By setting an extension length of the gasket 5 in a left-right direction as illustrated in FIG. 4 to be not smaller than a length of the mated first test sample 2 and second test sample 3, the gasket 5 can better support the first test sample 2 and the second test sample 3, so as to facilitate an observation of the process of the fretting fatigue damage of the first test sample 2 and the second test sample 3 in the high temperature environment.

In an embodiment, as illustrated in FIGS. 7 to 10, the gasket 5 may include two supporting portions 51 spaced apart from each other along the length direction of the first test sample 2 and the second test sample 3, and an interconnecting portion 52 connected to the two supporting portions 51. One of the two supporting portions 51 is located at an end of the first test sample 2 facing away from the second test sample 3, and the other one of the two supporting portions 51 is located at an end of the second test sample 3 facing away from the first test sample 2. The first test sample 2 and the second test sample 3 are placed on the interconnecting portion 52. It can be appreciated that one of the two supporting portions 51 can support the end of the first test sample 2 facing away from the second test sample 3, the other one of the two supporting portions 51 can support the end of the second test sample 3 facing away from the first test sample 2, and the interconnecting portion 52 can support portions of the first test sample 2 and the second test sample 3 located on the interconnecting portion 52. Consequently, the first test sample 2 and the second test sample 3 can be stably supported by the gasket 5.

In an embodiment, a distance between the two supporting portions 51 is greater than a distance between two ends where the clamping device clamps the first test sample 2 and the second test sample 3. It should be explained that a position where the clamping device clamps the first test sample 2 may be defined as a first end point, and a position where the clamping device clamps the second test sample 3 may be defined as a second end point. A distance between the first end point and the second end point is the distance between the two ends where the clamping device clamps the first test sample 2 and the second test sample 3. Here, the distance between the two supporting portions 51 is greater than the distance between the first end point and the second end point. During the experiment, when the clamping device clamps the first test sample 2 and the second test sample 3, the first test sample 2 and the second test sample 3 are required to be pulled away from each other. Since the distance between the two supporting portions 51 is greater than the distance between the first end point and the second end point, the clamping device can be prevented from colliding with the supporting portion 51, thereby avoiding damages of the supporting portion 51 or damages of the clamping device. In this way, the experiment may be carried out normally.

Figure 9:
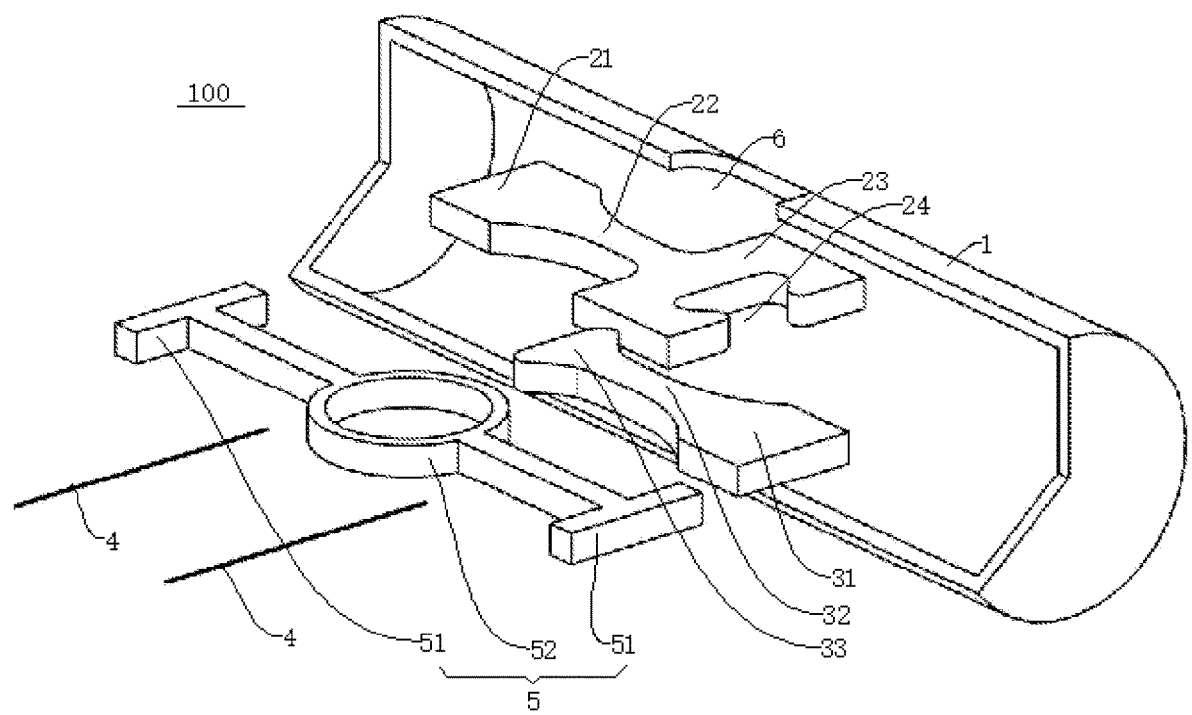
FIG. 9 is an exploded view of a system for ultra-high temperature in-situ fretting fatigue experiment according to another embodiment of the present disclosure.
Figure 10:
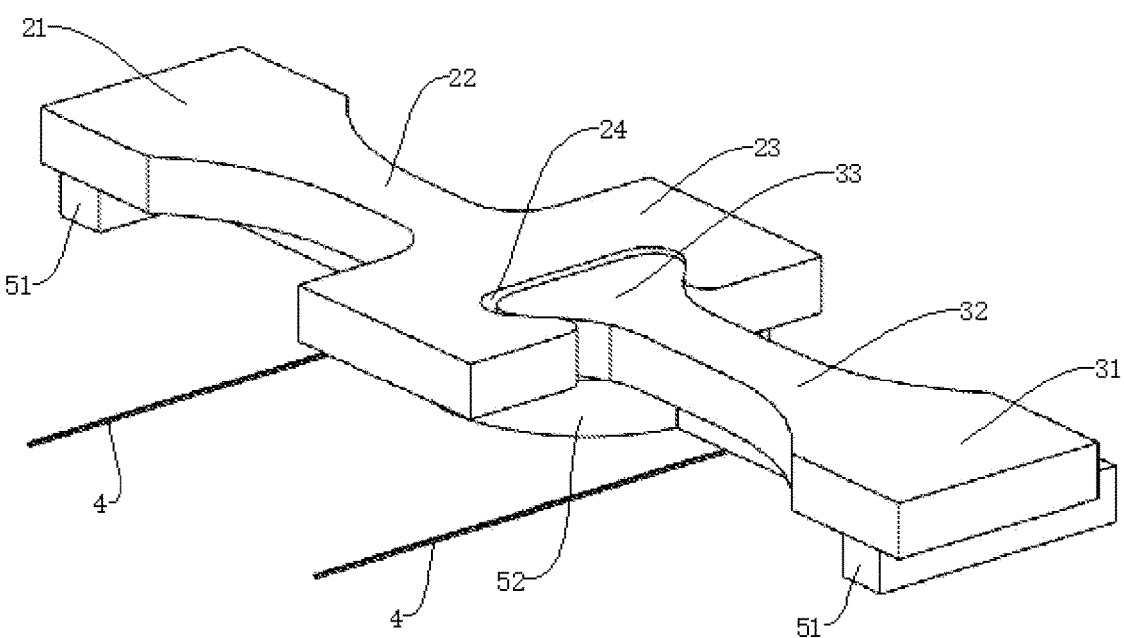
FIG. 10 is a schematic structural diagram of a first test sample, a second test sample, a heating wire, and a gasket according to another embodiment of the present disclosure.

In an embodiment, in conjunction with FIG. 9, the interconnecting portion 52 is formed as a hollow ring shape located at a position where the first test sample 2 and the second test sample 3 are mated with each other. It should be understood that the two symmetrical contact regions between the mortise 24 and the tenon 33 are regions to be observed. By observing these regions, the evolutionary process of the fretting fatigue damage of the first test sample 2 and the second test sample 3 in the high temperature environment can be observed. Here, a portion where the first test sample 2 and the second test sample 3 are mated with each other may refer to a portion where the mortise 24 and the tenon 33 are mated with each other. A ring-shaped hollow portion may avoid the portion where the mortise 24 and the tenon 33 are mated with each other, so as to reduce the interference to the two symmetrical contact regions of the mortise 24 and the tenon 33, thereby improving the accuracy of the experimental results. Further, the gasket 5 is made of a special high-temperature resistant material. That is, the gasket 5 can be composed of the high-temperature resistant material. After the heating wire 4 is heated, the gasket 5 can transfer heat to the first test sample 2 and the second test sample 3, and the material thereof emits few hot electrons and thus there are few hot electrons in the high temperature environment, thereby improving the imaging clarity of the observation instrument such as the SEM at high temperature. In addition, the gasket 5 made of the special material, due to the good wear resistance, corrosion resistance and thermal stability of the special material, has high stability in the high temperature environment and good thermal conductivity, allowing the experimental data to be more accurate. For example, the special material may be a ceramic material or other high-temperature resistant materials, which is not limited to these examples, as long as the materials meet practical requirements.

In some embodiments of the present disclosure, in a length direction of the heat preservation cover 1, a length of the first test sample 2 is equal to a length of the second test sample 3. Therefore, the contact portion of the mortise 24 and the tenon 33 is located right below the observation hole 6, such that the entire process of the fretting fatigue damage of the mortise 24 and the tenon 33 can be observed and recorded by SEM.

In addition, when the first test sample 2 is mated with the second test sample 3, clamps on left and right sides of the clamping device can clamp the first test sample 2 and the second test sample 3 symmetrically, allowing the clamping device to apply two symmetrical axis loadings. In this way, the loadings transmitted to the mortise 24 and the tenon 33 may be equal in magnitude and opposite in direction. As a result, the first friction surface 25 and the second friction surface 34 in the contact regions between the mortise 24 and the tenon 33 may be more stably contacted and generate friction, thereby producing the typical fretting fatigue condition.

In some embodiments of the present disclosure, the system for ultra-high temperature in-situ fretting fatigue experiment 100 further includes an SEM observation cavity and a vacuum device. The vacuum device is configured to form a vacuum state in the SEM observation cavity.

Figure 6:
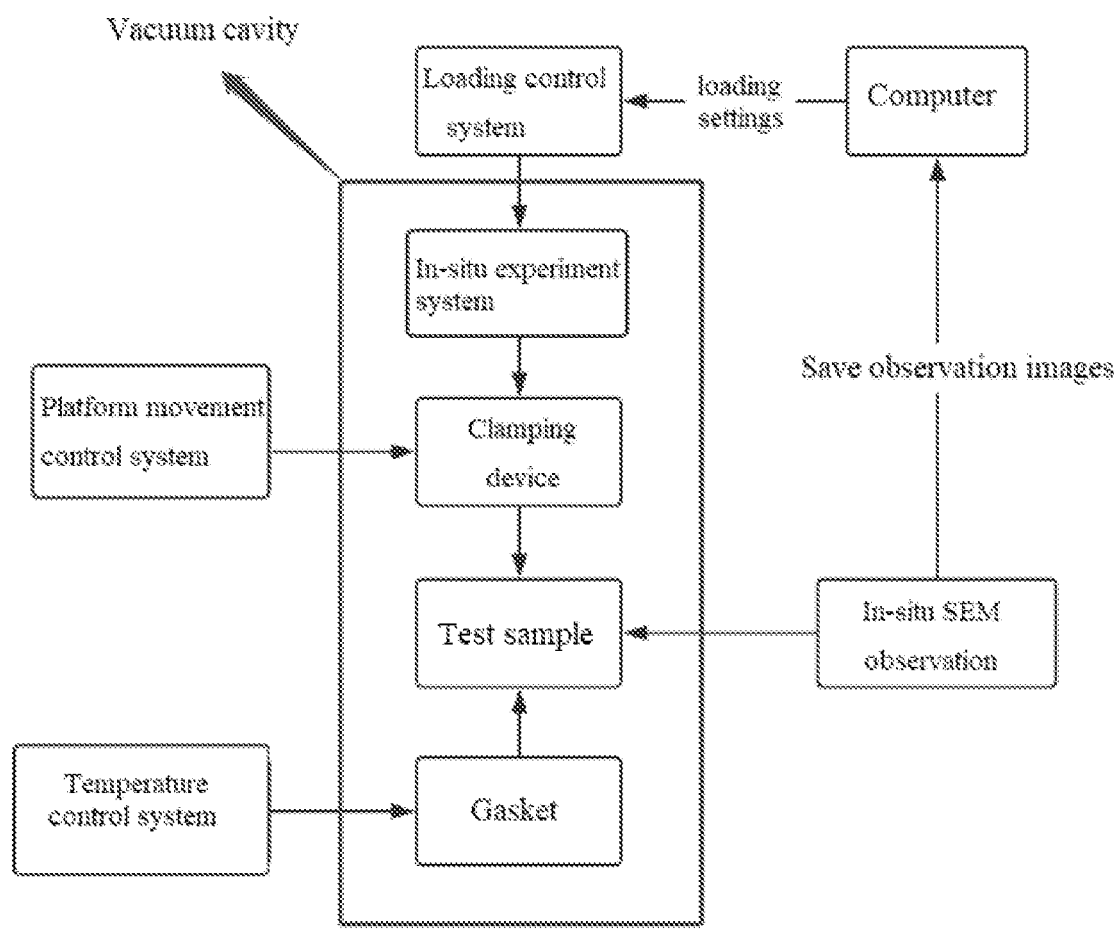
FIG. 6 is a flowchart of an experimental process of a system for ultra-high temperature in-situ fretting fatigue experiment according to an embodiment of the present disclosure.
Figure 7:
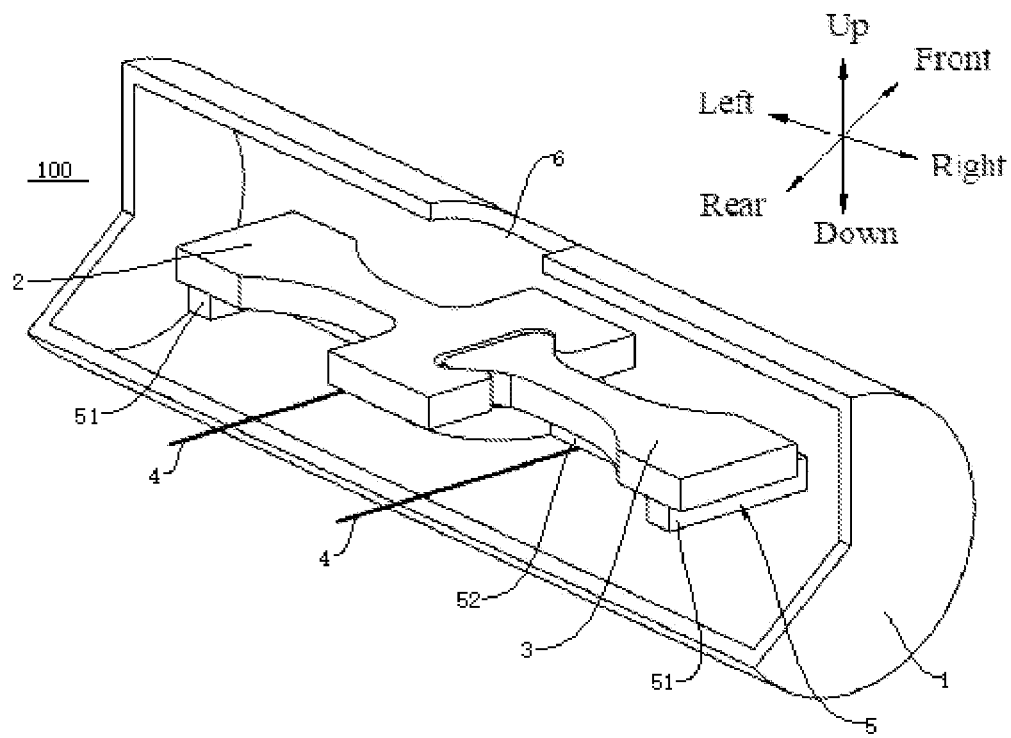
FIG. 7 is a schematic structural diagram of a system for ultra-high temperature in-situ fretting fatigue experiment according to another embodiment of the present disclosure.
Figure 8:
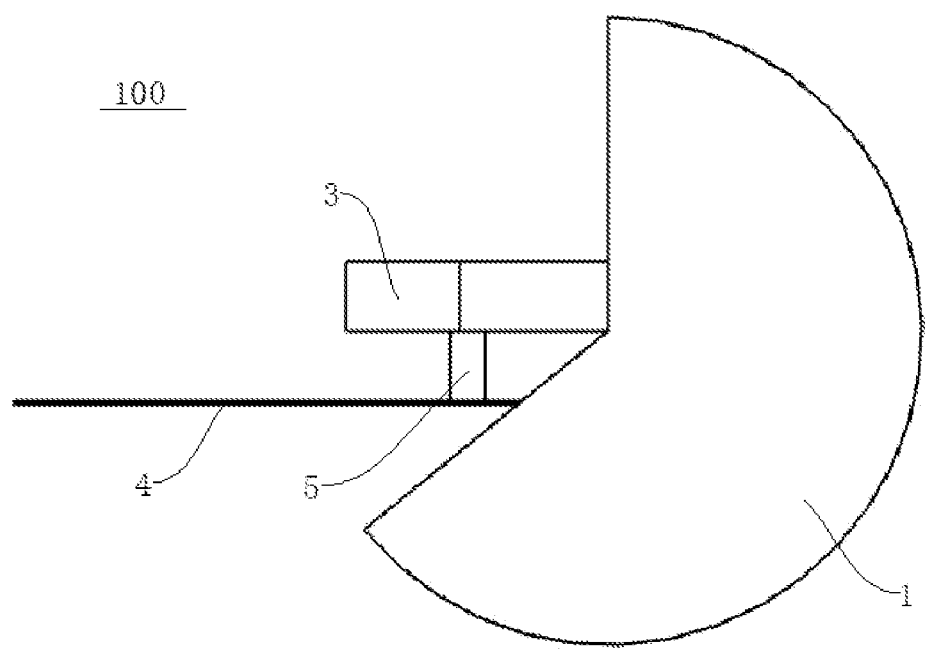
FIG. 8 is a schematic structural diagram, observing from another angle, of a system for ultra-high temperature in-situ fretting fatigue experiment according to another embodiment of the present disclosure.

For example, as illustrated in FIG. 6, during the experiment, the first test sample 2 and the second test sample 3 are mated with each other and placed on the gasket 5, and then placed on the heating device. The entire assembled device is pushed into the SEM observation cavity. Then the SEM observation cavity is sealed. After sealing, the SEM observation cavity can be placed in the vacuum device. The vacuum device is turned on to keep the entire cavity in the vacuum state. The heating device is activated such that the temperature control device can heat the heating wire 4 to allow the temperature in the SEM observation cavity to reach a set temperature. The vacuum device can prevent heat in the SEM observation cavity from being transferred outwardly, thereby maintaining a condition of the high temperature environment of the experiment. Then a hydraulic servo system is turned on to control the clamping device to start applying reciprocating loadings. That is, a nickel-based superalloy fretting fatigue experiment at high temperature begins, while performing an in-situ SEM observation with a computer monitor. During the experiment, the moving handle can be controlled to transmit instructions through a platform movement control system, such that the clamping device can move once receiving the instructions to implement a translation of the first test sample 2 and the second test sample 3 on the clamping device. The translation here may be a fine adjustment to move the two symmetrical contact regions between the mortise 24 and the tenon 33 to right below the observation hole 6. As a result, the SEM observation can photograph and record the entire process of crack initiation and propagation of the first test sample 2 and the second test sample 3 in real time.

Those skilled in the art can obtain other structural examples and operations of the system for ultra-high temperature in-situ fretting fatigue experiment according to the embodiments of the present disclosure, which are not described in detail herein.

Throughout the specification, expressions such as "an embodiment," "some embodiments," "illustrative examples", "an example," "a specific example," or "some examples," mean that a particular feature, structure, material, or characteristic described in joint with the embodiment or example is included in at least one embodiment or example of the present disclosure. The above expressions throughout the specification are not necessarily referring to the same embodiment or example of the present disclosure. Furthermore, the particular features, structures, materials, or characteristics may be combined in any suitable manner in one or more embodiments or examples.

Those skilled in the art can understand that, changes, alternatives, and modifications can be made to the embodiments of present disclosure illustrated and described above without departing from spirit and principles of the present disclosure. The scope of the present disclosure is defined by the attached claims and its equivalents.

What is claimed is:

1. A system for ultra-high temperature in-situ fretting fatigue experiment, comprising:
    a heat preservation cover defining a mounting space;
    a heating device arranged in the mounting space;
    a first test sample made of a nickel-based polycrystal superalloy and configured to simulate a turbine disk;
    a second test sample made of a nickel-based single-crystal superalloy and configured to simulate a turbine blade, wherein the first test sample and the second test sample are arranged at an upper end of the heating device along a horizontal direction, a mortise is formed at an end of the first test sample facing towards the second test sample, and a tenon configured to mate with the mortise is formed at an end of the second test sample facing towards the first test sample; and
    a clamping device arranged in the mounting space, wherein the clamping device is configured to be clamped at two ends of the mated first test sample and second test sample, and configured to apply a periodically reciprocating loading along a length direction of the first test sample and the second test sample,
    wherein the heating device comprises a heating wire and a gasket, the first test sample and the second test sample are disposed on the gasket, the gasket is configured to transfer heat generated by the heating wire towards the first test sample and the second test sample, and the heating wire is arranged at a lower end of the gasket; and
    wherein an observation hole in communication with the mounting space is defined on the heat preservation cover, the observation hole is located in a middle part of a length direction of the heat preservation cover, and the first test sample and the second test sample are mated with each other and movably arranged in the mounting space in such a manner that the mortise and the tenon are located right below the observation hole.

2. The system for ultra-high temperature in-situ fretting fatigue experiment according to claim 1, wherein, in a direction from the first test sample towards the second test sample, the first test sample sequentially comprises a first clamping portion, a first connecting portion, and a first mating portion; and
    wherein a width of the first connecting portion is smaller than a width of the first clamping portion and a width of the first mating portion, and the mortise is formed on the first mating portion to open towards the second test sample.

3. The system for ultra-high temperature in-situ fretting fatigue experiment according to claim 1, wherein, in a direction from the second test sample towards the first test sample, the second test sample sequentially comprises a second clamping portion, a second connecting portion, and a second mating portion; and
    wherein a width of the second connecting portion is smaller than a width of the second clamping portion and a width of the second mating portion, and the second mating portion is formed by the tenon.

4. The system for ultra-high temperature in-situ fretting fatigue experiment according to claim 1, wherein the heating device comprises a temperature control device,
    wherein the temperature control device is configured to adjust a temperature of the heating wire.

5. The system for ultra-high temperature in-situ fretting fatigue experiment according to claim 1, wherein in a length direction of the heat preservation cover, a length of the gasket is greater than or equal to a total length of the mated first test sample and second test sample.

6. The system for ultra-high temperature in-situ fretting fatigue experiment according to claim 1, wherein the gasket comprises two supporting portions spaced apart from each other along the length direction of the first test sample and the second test sample, and an interconnecting portion connected to the two supporting portions; and
    wherein one of the two supporting portions is located at an end of the first test sample facing away from the second test sample, the other one of the two supporting portions is located at an end of the second test sample facing away from the first test sample, and the first test sample and the second test sample are disposed on the interconnecting portion.

7. The system for ultra-high temperature in-situ fretting fatigue experiment according to claim 6, wherein the interconnecting portion is formed as a hollow ring located at a position where the first test sample and the second test sample are mated with each other.

8. The system for ultra-high temperature in-situ fretting fatigue experiment according to claim 1, wherein the gasket is made of a special high-temperature resistant material.

9. The system for ultra-high temperature in-situ fretting fatigue experiment according to claim 1, wherein in a length direction of the heat preservation cover, a length of the first test sample is equal to a length of the second test sample.

10. The system for ultra-high temperature in-situ fretting fatigue experiment according to claim 1, further comprising a scanning electron microscope (SEM) observation cavity and a vacuum device, wherein the vacuum device is configured to form a vacuum state in the SEM observation cavity.

* * * * *